(12) United States Patent
Irwin et al.

(10) Patent No.: US 11,103,378 B2
(45) Date of Patent: Aug. 31, 2021

(54) PALATE RETAINER WITH ATTACHED NASOPHARYNGEAL AIRWAY EXTENDER FOR USE IN THE TREATMENT OF OBSTRUCTIVE SLEEP APNEA

(71) Applicant: LUMEN DEVICES LLC, Greenwich, CT (US)

(72) Inventors: John N. Irwin, Greenwich, CT (US); Michael Friedman, Lincolnwood, IL (US); J. Christopher Flaherty, Auburndale, FL (US)

(73) Assignee: Lumen Devices, LLC, Greenwich, CT (US)

( * ) Notice: Subject to any disclaimer, the term of this patent is extended or adjusted under 35 U.S.C. 154(b) by 451 days.

(21) Appl. No.: 16/007,549

(22) Filed: Jun. 13, 2018

(65) Prior Publication Data

US 2018/0353322 A1    Dec. 13, 2018

Related U.S. Application Data

(63) Continuation of application No. 13/120,964, filed as application No. PCT/US2009/059333 on Oct. 2, 2009, now Pat. No. 10,022,262.

(60) Provisional application No. 61/194,956, filed on Oct. 2, 2008.

(51) Int. Cl.
*A61F 5/56* (2006.01)

(52) U.S. Cl.
CPC ......... *A61F 5/566* (2013.01); *Y10T 29/49826* (2015.01)

(58) Field of Classification Search
CPC ...................................................... A61F 5/566
See application file for complete search history.

(56) References Cited

U.S. PATENT DOCUMENTS

| | | | |
|---|---|---|---|
| 3,132,647 A | 5/1964 | Corniello | |
| 4,598,707 A | 7/1986 | Agdanowski et al. | |
| 4,669,459 A | 6/1987 | Spiewak et al. | |
| 4,778,448 A | 10/1988 | Meer | |
| 4,883,465 A | 11/1989 | Brennan | |
| 4,901,737 A | 2/1990 | Toone | |

(Continued)

FOREIGN PATENT DOCUMENTS

| | | |
|---|---|---|
| DE | 19501363 | 9/1995 |
| EP | 0418391 | 3/1991 |

(Continued)

OTHER PUBLICATIONS

Australian Office Action dated Mar. 28, 2014 issued in corresponding Australian Application No. 2009298395.

(Continued)

*Primary Examiner* — Daniel L Cerioni
(74) *Attorney, Agent, or Firm* — Onello & Mello, LLP

(57) ABSTRACT

A medical appliance for the treatment of obstructive sleep apnea in a patient, the appliance comprising: a securing device configured to be removably affixed to the patient's jaw; and a biasing member which is insertable behind the soft palate and/or the base of the patient's tongue, thereby providing for the flow of air in the nasopharyngeal airway; wherein the securing device is connected to the biasing member to allow insertion and/or removal of the biasing member from the nasopharyngeal airway.

21 Claims, 16 Drawing Sheets

(56) References Cited

U.S. PATENT DOCUMENTS

| | | | |
|---|---|---|---|
| 5,092,346 A | 3/1992 | Hays et al. | |
| 5,103,807 A | 4/1992 | Makaran | |
| 5,352,209 A | 10/1994 | Bird et al. | |
| 5,395,309 A | 3/1995 | Tanaka et al. | |
| 5,403,980 A | 4/1995 | Eckrich | |
| 5,938,582 A | 8/1999 | Ciamacco, Jr. et al. | |
| 6,048,073 A | 4/2000 | Shiao | |
| 6,102,929 A | 8/2000 | Conway et al. | |
| 6,117,386 A | 9/2000 | Stiger | |
| 6,273,859 B1 * | 8/2001 | Remmers | A61F 5/566 |
| | | | 600/529 |
| 6,275,724 B1 | 8/2001 | Dickinson et al. | |
| 6,312,138 B1 | 11/2001 | Coleman, Jr. et al. | |
| 6,394,093 B1 | 5/2002 | Lethi | |
| 6,408,852 B2 | 6/2002 | Tielemans | |
| 6,591,049 B2 | 7/2003 | Williams et al. | |
| 6,605,056 B2 | 8/2003 | Eidenschink et al. | |
| 6,734,893 B1 * | 5/2004 | Hess | A61B 1/2673 |
| | | | 348/65 |
| 6,770,263 B1 | 8/2004 | Brucker | |
| 6,916,287 B2 | 7/2005 | Dematteis et al. | |
| 6,955,172 B2 | 10/2005 | Nelson et al. | |
| 7,278,751 B2 | 10/2007 | Chang et al. | |
| 7,347,209 B2 | 3/2008 | Bovo | |
| 7,381,222 B2 | 6/2008 | Pflueger et al. | |
| 7,410,480 B2 | 8/2008 | Muni et al. | |
| 7,451,766 B2 | 11/2008 | Miller | |
| 7,547,296 B2 | 6/2009 | Lampropoulos et al. | |
| 7,654,997 B2 | 2/2010 | Makower et al. | |
| 7,658,192 B2 | 2/2010 | Harrington | |
| 7,686,021 B2 | 3/2010 | Knudson et al. | |
| 7,686,824 B2 | 3/2010 | Konstantino et al. | |
| 7,771,447 B2 | 8/2010 | Kunis | |
| 7,810,176 B2 | 10/2010 | Turner | |
| 7,815,661 B2 | 10/2010 | Mirizzi et al. | |
| 7,834,287 B2 | 11/2010 | Heiman et al. | |
| 7,861,722 B2 | 1/2011 | Keropian | |
| 7,879,061 B2 | 2/2011 | Keith et al. | |
| 7,887,661 B2 | 2/2011 | Chiu et al. | |
| 7,914,468 B2 | 3/2011 | Shalon et al. | |
| 8,127,769 B2 | 3/2012 | Walker | |
| 8,146,600 B2 | 4/2012 | Pflueger et al. | |
| 8,302,609 B2 | 11/2012 | Martinez | |
| 8,403,881 B2 | 3/2013 | Ferren et al. | |
| 8,678,008 B2 | 3/2014 | Rousseau et al. | |
| 8,684,007 B2 | 4/2014 | Timmons | |
| 8,739,794 B2 | 6/2014 | Cutler | |
| 8,894,614 B2 | 11/2014 | Muni et al. | |
| 8,978,647 B2 | 3/2015 | Djupesland et al. | |
| 9,132,028 B2 | 9/2015 | Friedman et al. | |
| 9,526,856 B2 | 12/2016 | Azagury et al. | |
| 9,668,911 B2 | 6/2017 | Flaherty et al. | |
| 10,022,262 B2 | 7/2018 | Irwin et al. | |
| 10,441,457 B2 | 10/2019 | Friedman et al. | |
| 10,660,787 B2 | 5/2020 | Flaherty et al. | |
| 2001/0027793 A1 | 10/2001 | Tielemans | |
| 2002/0009275 A1 | 1/2002 | Williams et al. | |
| 2003/0014007 A1 | 1/2003 | Eidenschink et al. | |
| 2003/0121519 A1 * | 7/2003 | Estes | A61M 16/0069 |
| | | | 128/204.18 |
| 2004/0020492 A1 | 2/2004 | Dubrul et al. | |
| 2004/0049102 A1 | 3/2004 | Nelson et al. | |
| 2004/0138585 A1 | 7/2004 | Dematteis et al. | |
| 2004/0143287 A1 | 7/2004 | Konstantino et al. | |
| 2004/0194785 A1 | 10/2004 | Miller | |
| 2005/0137618 A1 | 6/2005 | Kunis | |
| 2005/0203366 A1 | 9/2005 | Donoghue et al. | |
| 2005/0240147 A1 | 10/2005 | Makower et al. | |
| 2005/0268919 A1 | 12/2005 | Knudson et al. | |
| 2006/0064037 A1 | 3/2006 | Shalon et al. | |
| 2006/0106361 A1 | 5/2006 | Muni et al. | |
| 2006/0130850 A1 | 6/2006 | Chen | |
| 2006/0169285 A1 | 8/2006 | Bovo | |
| 2006/0195135 A1 | 8/2006 | Ayoub | |
| 2006/0229669 A1 | 10/2006 | Mirizzi et al. | |
| 2007/0008715 A1 | 1/2007 | Chang et al. | |
| 2007/0066942 A1 | 3/2007 | Lampropoulos et al. | |
| 2007/0103451 A1 | 5/2007 | Heiman et al. | |
| 2007/0129751 A1 | 6/2007 | Muni et al. | |
| 2007/0255198 A1 | 11/2007 | Leong et al. | |
| 2008/0015497 A1 | 1/2008 | Keith et al. | |
| 2008/0035158 A1 | 2/2008 | Pflueger et al. | |
| 2008/0035160 A1 * | 2/2008 | Woodson | A61F 5/566 |
| | | | 128/860 |
| 2008/0041396 A1 | 2/2008 | Lucker | |
| 2008/0041516 A1 | 2/2008 | Chiu et al. | |
| 2008/0051871 A1 | 2/2008 | Tuch | |
| 2008/0058584 A1 | 3/2008 | Hirotsuka et al. | |
| 2008/0065209 A1 | 3/2008 | Pflueger et al. | |
| 2008/0076094 A1 * | 3/2008 | Hindin | A61C 13/0024 |
| | | | 433/215 |
| 2008/0078412 A1 | 4/2008 | Buscemi et al. | |
| 2008/0091067 A1 | 4/2008 | Dollar | |
| 2008/0210244 A1 | 9/2008 | Keropian | |
| 2008/0289637 A1 | 11/2008 | Wyss | |
| 2009/0084388 A1 | 4/2009 | Bagley et al. | |
| 2009/0157056 A1 | 6/2009 | Ferren et al. | |
| 2009/0204099 A1 | 8/2009 | Feloney | |
| 2009/0281433 A1 * | 11/2009 | Saadat | A61B 5/6839 |
| | | | 600/483 |
| 2010/0024830 A1 | 2/2010 | Rousseau et al. | |
| 2010/0198249 A1 | 8/2010 | Sabliere | |
| 2010/0211009 A1 | 8/2010 | Leonard et al. | |
| 2010/0268025 A1 | 10/2010 | Belson | |
| 2010/0282246 A1 | 11/2010 | Djupesland et al. | |
| 2010/0319708 A1 | 12/2010 | Mahr et al. | |
| 2011/0178439 A1 | 7/2011 | Irwin et al. | |
| 2011/0226264 A1 | 9/2011 | Friedman et al. | |
| 2013/0046329 A1 | 2/2013 | Burbank et al. | |
| 2013/0312768 A1 | 11/2013 | Flaherty et al. | |
| 2014/0000622 A1 | 1/2014 | Azagury et al. | |
| 2015/0342779 A1 | 12/2015 | Friedman et al. | |
| 2016/0001022 A1 | 1/2016 | Djupesland et al. | |
| 2017/0266034 A1 | 9/2017 | Flaherty et al. | |
| 2020/0306474 A1 | 10/2020 | Flaherty et al. | |

FOREIGN PATENT DOCUMENTS

| | | |
|---|---|---|
| EP | 2205306 | 7/2010 |
| WO | 2007020197 | 2/2007 |
| WO | 2008122791 | 10/2008 |
| WO | 2010068493 | 6/2010 |
| WO | 2014030078 | 2/2014 |

OTHER PUBLICATIONS

Canadian Office Action dated Aug. 4, 2015 issued in corresponding Canadian Application No. 2739292.

Canadian Office Action dated Feb. 9, 2018 issued in corresponding Canadian Application No. 2739292.

Canadian Office Action dated May 18, 2016 issued in corresponding Canadian Application No. 2739292.

European Office Action dated May 31, 2012 issued in corresponding European Application No. 09818548.1.

International Search report and Written Opinion dated Nov. 23, 2009 issued in corresponding International Application No. PCT/US2009/059333.

"A Palate Retainer With Attached Nasopharyngeal Airway Extender for Use in the Treatment of Obstructive Sleep Apnea" Specification, Drawings, and Prosecution History of U.S. Appl. No. 13/120,964, filed Mar. 25, 2011, now issued U.S. Pat. No. 10,022,262, issued on Jul. 17, 2018, by John N. Irwin, et al., which is stored in the United States Patent and Trademark Office (USPTO).

European Office Action dated Jan. 22, 2021 issued in corresponding European Application No. 15195168.8.

* cited by examiner

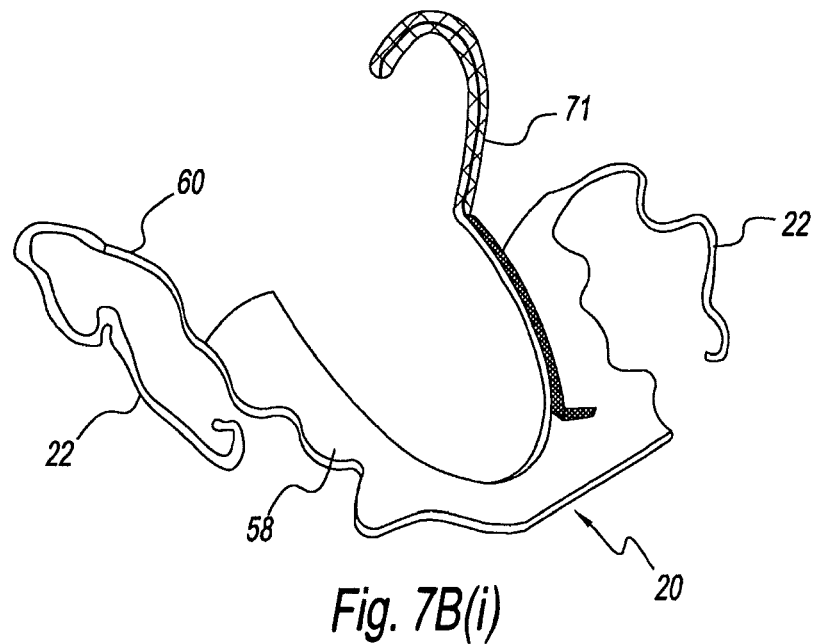
Fig. 7B(i)
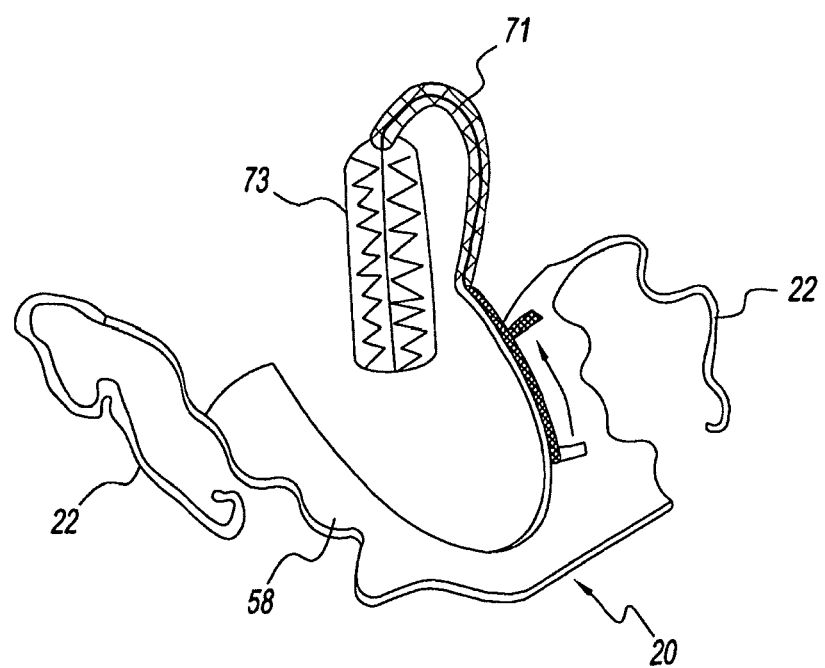
Fig. 7B(ii)

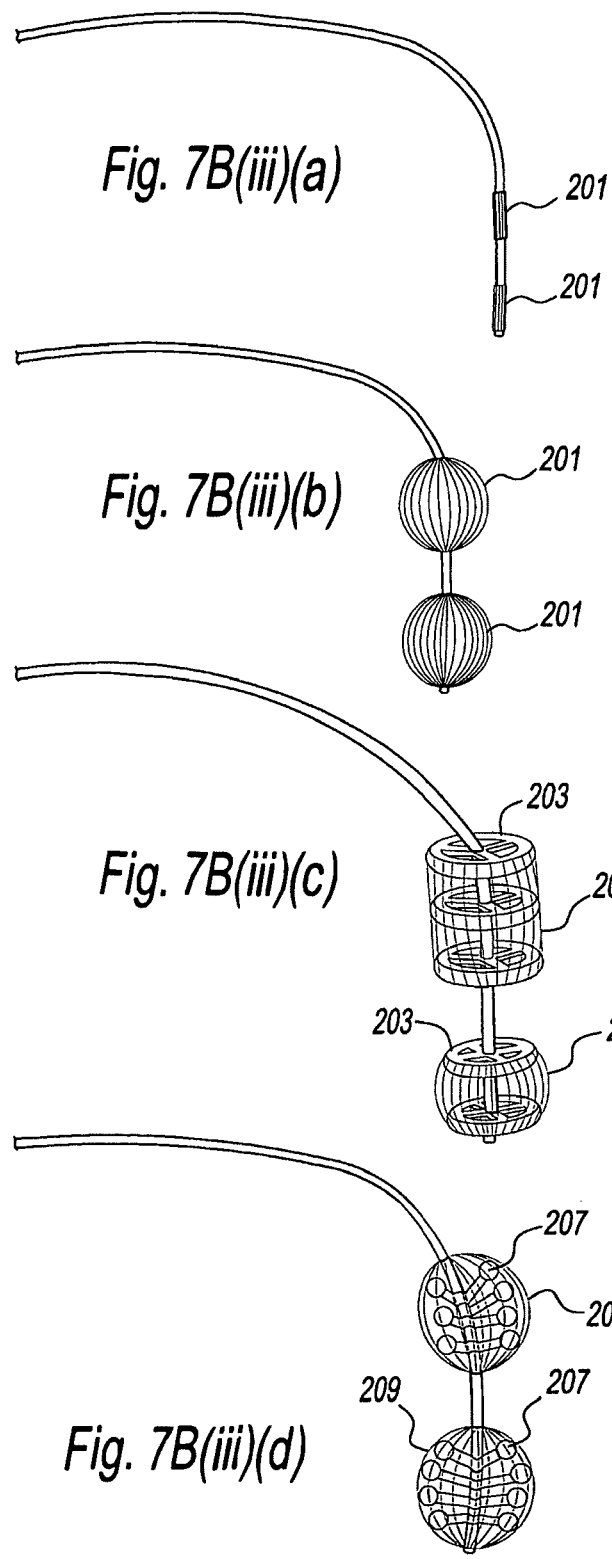

Fig. 7B(iv)

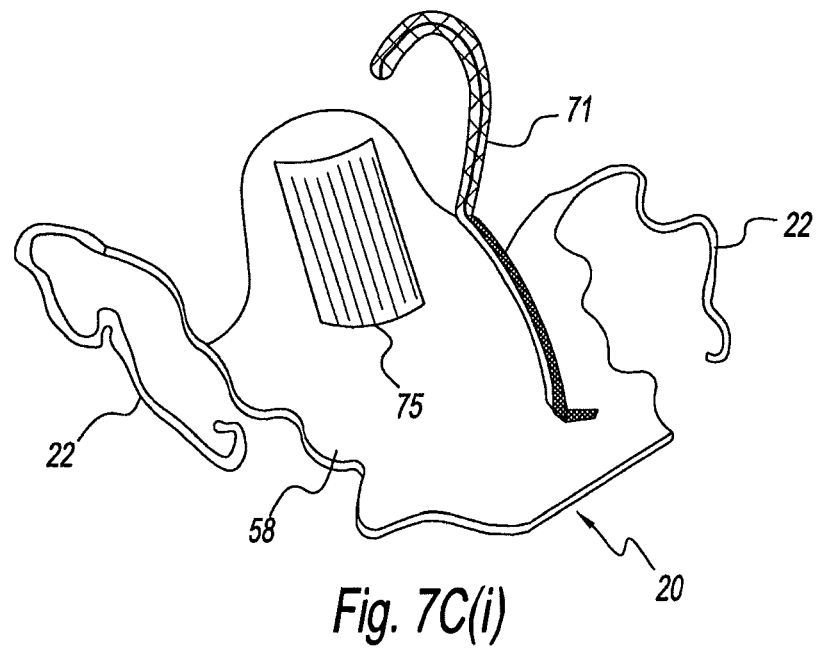
Fig. 7C(i)
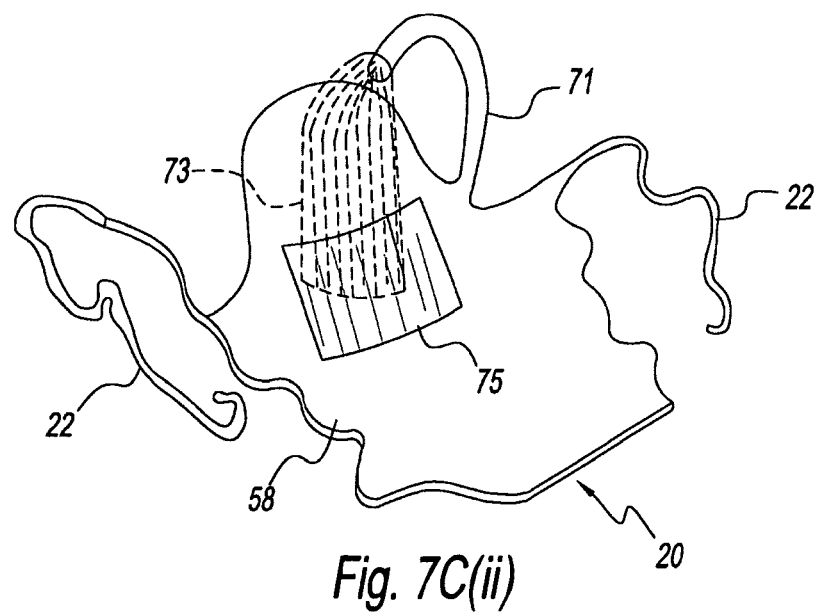
Fig. 7C(ii)

PALATE RETAINER WITH ATTACHED NASOPHARYNGEAL AIRWAY EXTENDER FOR USE IN THE TREATMENT OF OBSTRUCTIVE SLEEP APNEA

BACKGROUND

1. Field

The present disclosure relates generally to the use of an interoral appliance, such as a palate retainer configured with a nasopharyngeal extension. The nasopharyngeal extension is a tube or airway extender that fits behind the soft palate with the lumen large enough to allow adequate air to pass behind the soft palate in the nasopharynx. It may also be extended to pass upwards behind the soft palate and downwards behind the base of tongue.

2. Discussion of the Background Art

The sleep apnea syndrome, and in particular obstructive sleep apnea, afflicts an estimated 2-5% of the general population and is due to episodic upper airway obstruction during sleep. Those afflicted with obstructive sleep apnea experience sleep fragmentation and intermittent, complete or nearly complete cessation of ventilation during sleep with potentially severe degrees of oxy hemoglobin unsaturation. These features may be translated clinically into debilitating daytime sleepiness, cardiac disrhythmias, pulmonary-artery hypertension, congestive heart failure and cognitive dysfunction. Other problems related to sleep apnea include carbon dioxide retention during wakefulness as well as during sleep, and continuous reduced arterial oxygen tension. Hypersomnolent sleep apnea patients may be at risk for excessive mortality from these factors as well as from an elevated risk for accidents such as while driving or operating other potentially dangerous equipment.

Although details of the pathogenesis of upper airway obstruction in sleep apnea patients have not been fully defined, it is generally accepted that the mechanism includes either anatomic or functional abnormalities of the upper airway which result in increased air flow resistance. Such abnormalities may include narrowing of the upper airway due to suction forces evolved during inspiration, the effect of gravity pulling the tongue back to appose the pharyngeal wall, and/or insufficient muscle tone in the upper airway dilator muscles. It has also been hypothesized that a mechanism responsible for the known association between obesity and sleep apnea is excessive soft tissue in the anterior and lateral neck which applies sufficient pressure on internal structures to narrow the airway.

One theory of the cause for the sleep disturbance is the relaxation of the tongue and pharyngeal walls to varying degrees during the several stages of sleep. When fully awake, these tissues have normal tone as air passes in and out of the lungs during respiration. However, during sleep, the musculature supporting these tissues relaxes. As air is inspired, the tongue and posterior walls of the pharynx collapse, causing snoring or more seriously causing partial or complete obstruction of the airway.

Obstructive sleep apnea occurs due to a collapse of soft tissue within the upper airway during sleep. The ongoing force of inspiration serves to generate increasingly negative pressure within the pharynx, causing further collapse. The lack of respiration results in inadequate blood oxygenation, and rising carbon dioxide levels. The cardiovascular response produces an increase in the blood pressure and pulse, and cardiac arrhythmias often occur. The carbon dioxide increase and oxygen desaturation triggers a transition to a lighter sleep stage, usually without wakefulness. This transition brings a return to tonicity of the muscles of the upper airway, allowing normal breathing to resume. The person then returns to deeper stages of sleep and the process is repeated. The disease is quantified in terms of respiratory disturbances per hour. Mild disease begins at 2-3 APNEAS per hour, and it is not uncommon to find patients with indices of about one hundred or more.

Not surprisingly, sleep is extremely fragmented and of poor quality in persons suffering from sleep apnea. As a result, such persons typically feel tired upon wakening and may fall asleep at inappropriate times during the day. All aspects of quality of life, from physical and emotional health, to social functioning are impaired by obstructive sleep apnea.

Surgical Treatments

The treatment of sleep apnea has included such surgical interventions as Uvulopalatopharyngoplasty (UPPP) gastric surgery for obesity, and maxillo-facial reconstruction. Another mode of surgical intervention used in the treatment of sleep apnea is tracheostomy. These treatments constitute major undertakings with considerable risk of post-operative mortality. In UPPP, any remaining tonsil tissue and a portion of soft palate is removed. The procedure often increases the nasopharyngeal airway. However, UPPP does not always fix a sagging soft palate nor does it address apnea caused by obstructions caused by the base of the tongue being deeper in the oropharynx part of the airway. These surgical techniques are extremely invasive, requiring general anesthesia, and a prolonged, painful recovery.

LAUP, or Laser-Assisted Uvulopalatoplasty, is a modification of the above-mentioned technique, but has had mixed success and cannot solve obstructions in the foropharynx part of the airway or sleep apnea.

Radio frequency tissue ablation (RFTA) with the trade name "Somnoplasty," has been used to shrink the soft palate, uvula and reduce tongue volume in the treatment of snoring and obstructive sleep apnea. Somnoplasty utilizes a radiofrequency tool that generates heat to create coagulative lesions at specific locations within the upper airway. The lesions created by the procedure are naturally resorbed in approximately three to eight weeks, reducing excess tissue volume and increasing the airway opening. Like UPPP and LAUP, more than one session is typically required, and other surgeries may still be necessary in moderate to severe cases, and there are occasional problems with morbidity.

Another area of surgical interest lies in techniques designed to pull the tongue anteriorly. The most recent such surgical system designed to treat snoring (as well as obstructive sleep apnea) was approved by the FDA in February 1998. Known as the tongue suspension procedure (with the trade name Repose), it is intended to pull the tongue forward, thereby keeping the tongue from falling into the airway during sleep. The system utilizes a bone screw inserted into the mandible. The screw attaches to a nonabsorbable suture which travels the length of the tongue and back. Similarly, the hyoid bone can be drawn anteriorly with two distinct screws, also attached to the mandible.

Techniques have also been developed for treating, specifically, the condition of snoring. Conrad et al., U.S. Pat. No. 6,250,307 discloses a method for treating snoring of a patient, which includes embedding an implant into a soft palate of a patient in order to alter a dynamic response of a soft palate to airflow. The methods of Conrad et al. are specifically designed to reduce the audibility of snoring but do not address the more serious condition of sleep apnea.

These conventional treatments continue to suffer poor cure rates. The failures lie in their inability to maintain patency in the retropalatal region and retroglossal region (the caudal margin of the soft palate to the base of the epiglottis). The poor success rates combined with high morbidity from some of the surgical interventions, contribute to an ongoing need for more effective treatments for sleep apnea and/or snoring.

Pharmacological Treatments

Pharmacological therapy, aimed at stimulating upper airway muscle to reduce apneas, also have, in general, been disappointing. In addition, side effects from the pharmacological agents that have been used are frequent. Thus, medical practitioners continue to seek non-invasive modes of treatment for sleep apnea with high success rates and high patient compliance including, for example in cases of minor to moderate sleep apnea relating to obesity, weight loss through a regimen of exercise and regulated diet.

Other Non-Surgical Treatments

Other non-surgical treatments for sleep apnea include the use of oral devices and appliances that work to prevent the tongue from falling backwards or help reduce the collapse of the soft palate. Still other treatments involve the use of retainers that push the lower jaw forward, thereby pulling the tongue slightly forward and, in some cases, helping elevate the soft palate. Also, there are devices that pull on the tongue to keep it forward during sleep. These current oral devices typically do not create a significant improvement except in mild to moderate cases and can be associated with movement of the teeth over time of problems with the temporamandibular joint.

Recent work in the treatment of sleep apnea has included the use of continuous positive airway pressure (CPAP) to maintain the airway of the patient in a continuously open state during sleep. For example, U.S. Pat. No. 4,655,213 and Australian patent AU-B-83901/82 both disclose sleep apnea treatments based on continuous positive airway pressure applied within the airway of the patient.

Also of interest is U.S. Pat. No. 4,773,411 which discloses a method and apparatus for ventilatory treatment characterized as airway pressure release ventilation and which provides a substantially constant elevated airway pressure with periodic short term reductions of the elevated airway pressure to a pressure magnitude no less than ambient atmospheric pressure.

Although CPAP has been found to be very effective and well accepted, it suffers from some of the same limitations, although to a lesser degree, as do the surgical options; specifically, a significant proportion of sleep apnea patients do not tolerate CPAP well. Thus, development of other viable non-invasive therapies has been a continuing objective in the art.

Still others have attempted to solve sleep apnea disorders using intraorally fitted appliances, including U.S. Pat. Nos. 4,981,437 and 4,932,867, that disclose a method and apparatus for constructing dentures, which are useful, for example, in treating breathing disorders. U.S. Pat. No. 4,386,405 discloses a device for measuring the location, attitude, or change of location of a patient's lower jaw. U.S. Pat. No. 4,859,181 relates to optical measurement of jaw movement. U.S. Pat. Nos. 3,998,209 and 4,220,142 disclose conditioning systems for use in a program of behavior modification to eliminate snoring, while U.S. Pat. No. 4,976,618 relates to treatment of temporomandibular joint dysfunction and bruxism. U.S. Pat. No. 3,297,021 discloses an intraoral strain gauge and telemetering of information from an intraoral location to an outside indicator.

The following U.S. patents purport to relate to tongue positioning and/or retaining apparatus: U.S. Pat. Nos. 5,154,184, 5,092,346, 5,046,512, 4,676,240, 4,169,473, 4,304,227 and 4,593,686. Other patents addressing the matter of tongue positioning include the following: U.S. Pat. Nos. 5,649,540, 5,465,734, 5,373,859, 5,052,409, 4,715,368, 4,196,724, 3,884,226, 3,312,216 and 3,132,647, as well as European Patent 0182387 and British Patent 874,480. The following patents purport to relate to chin straps or similar apparatus intended to hold the jaw closed: U.S. Pat. Nos. 3,312,217, 2,711,730 and 1,990,411.

Other patents relate to apparatus for interaction with the soft palate in the user's oral cavity. These include U.S. Pat. Nos. 4,669,459 and 5,316,020, German patent no. DE 40 26 602 and European patent no. EP 0264516. Other patents of general interest include U.S. Pat. Nos. 5,056,534 and 2,705,006, German patent nos. 65194 and 2320501, and PCT publication no. WO 92/05752 and European patent application no. 0 487 469 A1.

While the above-identified conventional devices and surgical techniques are purported to treat upper airway instability, such as OSA or snoring, they are successful, if at all, in only a limited pool of patients or under limited circumstances. Therefore, there remains a relatively large number of patients whose airway disorder is believed to be treatable using an intraoral appliance, yet conventional appliances are ineffective, overly burdensome, uncomfortable, or any combination thereof.

The present disclosure overcomes the aforementioned disadvantages of the prior art by using a novel palate retainer with a nasopharyngeal extension, wherein the nasopharyngeal extension fits behind the soft palate with a tube that has a lumen large enough to allow for the passage of air in the nasopharynx.

The present disclosure also provides many additional advantages, which shall become apparent as described below.

SUMMARY

The present disclosure pertains to methods and/or medical appliances or devices which are preferably attached to the upper or lower jaws, for entering the mouth horizontally with a compressed device, in a way that minimizes triggering the gag reflex of a patient, and then having part of the device (e.g., a tube or two tubes on the side or some other kind of expander for the airway) go vertical (i.e. in a superior direction)—up behind the soft palate and/or down (i.e. in an inferior direction) behind part of the tongue. It is preferable, to provide a device which allows for further expansion of the tube or tubes once in place in the airway, in a way that still allows for swallowing.

A novel palate retainer with a nasopharyngeal extension, that fits behind the soft palate with a tube or other airway extender that has a lumen large enough to allow for the passage of air in the nasopharynx and behind the tongue. In particular, the palate retainer is designed to be secured to the upper palate of a patient's jaw, similar to a retainer device, so as to position the nasopharyngeal extension, e.g., a tube or other airway expander, behind the soft palate. This tube or spacer is designed to protrude from the posterior end of the palatal retainer. This tube is typically connected to the retainer by a connecting collar portion which slips underneath the soft palate and the tube ends up behind the soft palate. The tube is preferably relatively short in length during placement, but could be expanded after placement. This appliance would physically splint the palate and the tongue and prevent the palate from falling back, help stabilize the tongue and at the same time, provide a rigid airway in the retropalatal and retrolinqual space that cannot collapse.

The tube can have a round cross-section or be flatter and wider, similar to a wide soft palate, as that shape could be more tolerable for the patient, particularly during swallowing. Alternatively, the tube can have a section that is a compressed flexible tube, with several hard plastic rings which help prevent collapse of the flexible tube. This tube configuration can attached to the top of a rigid tube and, once in place behind the soft palate, can be released to spring upwards or downwards (if attached to the bottom of the rigid tube, as needed. It is preferably, that the tube be partially flexible to allow for extraction after use. The bottom tube could also be a firm tube that fits within the attached tube and then falls downward from gravity or is has a small spring that, when released, pushes this inner section of the tube downwards. If the bottom extension is a firm tube, then it is preferable that the tube be flexible where it joins the firm tube on the retainer, so as to allow for extraction by bending during extraction, after it has been expanded downward in place behind the base of tongue.

Yet another embodiment comprises two tubes on either side, held behind the soft palate.

Still another embodiment involves the attached tube or airway expander which has a compressed diameter which expands once in place—so as to allow an easier entry in some patients.

Furthermore, the present disclosure is a palate retainer having only one ribbon-like extension that bends behind, below and behind, the soft palate that holds the rigid tube or that it might not hold the tube, but simply be a curved hollow ribbon that allows a device to be pushed behind the soft palate, expanding as it leaves the tube. Or a bendable tube could be attached on a track alongside the ribbon-like extension, and could be pushed alongside and behind the soft palate.

The present disclosure provides a novel medical appliance for the treatment of obstructive sleep apnea in a patient, the appliance comprising: a securing device configured to be removably affixed to the patient's jaw; and a biasing member which is insertable behind the soft palate and/or the base of the patient's tongue, thereby providing for the flow of air in the nasopharyngeal airway; wherein the securing device is connected to the biasing member to allow insertion and/or removal of the biasing member from the nasopharyngeal airway.

The appliance further comprising a connector device disposed between the securing device and the biasing member. The biasing member comprises at least two concentric tubes, wherein a first concentric tube is disposed within a second concentric tube. The appliance further comprises a first actuator which expands the biasing member by causing the first concentric tube to move in a vertical direction away from the second concentric tube. Alternatively, the appliance further comprises a third concentric tube and a second actuator, wherein the first and second actuators can be either the same actuator or different actuators. Preferably, the first concentric tube moves in an upward vertical direction and the third concentric tube moves in a downward vertical directions away from the second concentric tube. The first concentric tube is formed of a mesh wire. Optionally, the appliance further comprises a locking mechanism which prevents the first concentric tube from collapsing back within the second concentric tube.

Optionally, the biasing member comprises at least one tube having either a circular or elliptical cross-section. The tube comprises a proximal end, a distal end and a lumen therethrough. Preferably, at least a portion of the tube comprises perforations to allow for air to pass therethrough. To provide structural integrity, the tube comprises at least one or more rings disposed about a diameter of the tube, thereby limiting compression of the tube.

The appliance further comprises a release device for causing the biasing member to unfold in a direction opposite to that of the biasing member when inserted behind the soft palate and/or the base of the patient's tongue.

Preferably, the securing device is a palate retainer. The securing device is attached to either the upper or lower jaw of the patient. The palate retainer comprises a molded insert and at least one connector used to connect the insert to the jaw. The connector is a wire securably mounted to at least one tooth of the jaw. Preferably, the molded insert is either continuous or non-continuous about the patient's palate.

The nasopharyngeal airway comprises a nasopharynx region and/or an oropharynx region.

Alternatively, the biasing member is at least one member selected from the group consisting of: a flexible or rigid stent, balloon, and combination thereof. Preferably, the stent is housed in a tube or ribbon, and further comprises an actuator to move the stent out of the housing. The stent is typically formed from either a metal or magnetic wire mesh. Optionally, at least one magnet can be disposed about the securing device and the biasing member is formed of a metal or other magnetic material, such that the biasing member is attracted to the magnetic force of the magnet in the securing device (e.g., palate retainer) such that the biasing member is pulled toward the magnet together with the soft palate or base of the tongue. Alternatively or additionally, the biasing member may include a magnet, and the securing device includes a magnetic portion attracted to the biasing member magnet.

Optionally, the biasing member expands either radially or longitudinally when in position behind the soft palate or base of the tongue. It is preferably that the biasing member include an adjuster which operably expands or contracts the biasing member in either the radial or longitudinal directions.

The connector device is removably disposed between the securing device and the biasing member. Preferably, the connector device is at least one selected from the group consisting of: a 'C' shaped neck, collar or ribbon, frictionally engaging surfaces, a snap fit assembly, a screw attached joint, hinged connector, and any combination thereto. The connector device applies a force to the biasing member to operably adjust from a first magnitude to a second magnitude. Preferably, adjustment occurs over time or as at least a portion of the biasing member transitions from a first temperature to a second temperature.

The hinged connector is preferably an adjustable force hinge. The hinged connector further comprises a locking device which operably prevent rotation of the hinged connector.

The appliance further comprises a force measurement assembly which measures the force exerted by the biasing member upon the soft palate or the base of tongue of the patient. The force measurement assembly is a force transducer selected from the group consisting of: a strain gauge, a magnetic sensor, a capacitive sensor, a piezo transducer and a combination thereof.

The appliance further comprises a force monitor assembly which monitors the forces recorded by the force measurement assembly to determine is the recorded force exceeds a threshold force.

The appliance further comprises a visualization assembly which provides an image of the area behind the soft palate and/or area behind the base of the tongue. The visualization assembly is integral to the biasing member, affixed to the securing device or an optical fiber which is passed through the patient's nasal passage. The visualization assembly comprising at least one fiber optic cable and at least one device selected from the group consisting of: a camera, a camera lens, and a ccd assembly.

A method for treating a patient having sleep apnea, the method comprising: inserting into a patient's mouth a medical appliance which comprises: a securing device configured to be removably affixed to the patient's jaw; and a biasing member which is insertable behind the soft palate and/or the base of the patient's tongue, thereby providing for the flow of air in the nasopharyngeal airway; wherein the securing device is connected to the biasing member to allow insertion and/or removal of the biasing member from the nasopharyngeal airway. The method further comprising: adjusting the size of the biasing member; adjusting the force applied by the biasing member; and/or adjusting the position of the biasing member relative to the securing device.

A method for diagnosing sleep apnea in a patient, the method comprising: inserting into a patient's mouth a medical appliance which comprises: a securing device configured to be removably affixed to the patient's jaw; and a biasing member which is insertable behind the soft palate and/or the base of the patient's tongue, thereby providing for the flow of air in the nasopharyngeal airway; wherein the securing device is connected to the biasing member to allow insertion and/or removal of the biasing member from the nasopharyngeal airway; and conducting at least one diagnostic procedure selected from the group consisting of: (a) measuring a force applied by the biasing member to the soft palate or base of tongue of the patient; (b) viewing the amount of contact between the biasing member and the soft palate or base of tongue of the patient; (c) inserting a visualization device into the mouth or nose of the patient, wherein the visualization device is configured to visualize the amount of contact between the biasing member and the soft palate or base of tongue of the patient; and (d) quantifying the size of the opening between the biasing member and the soft palate or base of the tongue of the patient.

A method of fabricating a medical application, the method comprising: producing a medical appliance which comprises: a securing device configured to be removably affixed to the patient's jaw; and a biasing member which is insertable behind the soft palate and/or the base of the patient's tongue, thereby providing for the flow of air in the nasopharyngeal airway; wherein the securing device is connected to the biasing member to allow insertion and/or removal of the biasing member from the nasopharyngeal airway; measuring a portion of a patient's oral cavity; and sizing the medical appliance to fit the measured oral cavity.

Further objects, features and advantages of the present disclosure will be understood by reference to the following drawings and detailed description.

BRIEF DESCRIPTION OF THE DRAWINGS

FIG. 7b(ii) depicts the stent of FIG. 7b(i) wherein the stent is in the exposed or expanded position, where, when attached to the upper jaw, the stent would expand upwards behind the soft palate from the tip of the curved hollow ribbon or tube;

FIGS. 7b(iii)(a)-(d) are various embodiments wherein the stent of FIG. 7b(i) is replaced with inflatable balloons or expandable wire balls;

FIG. 7b(iv) is another embodiment wherein the stent of FIG. 7b(i) is replaced with a memory wire which forms a spiral or helical configuration when exposed;

FIG. 7b(v) is another embodiment wherein the stent of FIG. 7b(i) is replaced with a memory wire which forms a loop or elliptical configuration when exposed;

FIG. 7c(i) is yet another embodiment of the present disclosure depicting a the stent of FIG. 7b(i) wherein the stent is formed of metal or magnetic wire mesh and wherein at least one magnet is disposed about the retainer portion (preferably after the metal or magnetic wire mesh is expanded from the hollow stent housing behind the soft palate), thereby allowing for the soft palate to be held in an opened position due to the magnetic force between the magnet on the retainer portion and the wire mesh expanded behind the soft palate;

FIG. 7c(ii) depicts the stent of FIG. 7c(i) wherein the stent is in the exposed or expanded position;

FIG. 7d is a cross-sectional view of an appliance according to the present disclosure according to another embodiment, wherein a palate retainer is a platform for both a fixed tube behind the soft palate and a downwardly expandable tube behind the base of a tongue, optionally, with an expansion bulb or the like;

DETAILED DESCRIPTION OF THE PREFERRED EMBODIMENT

Figure 1:
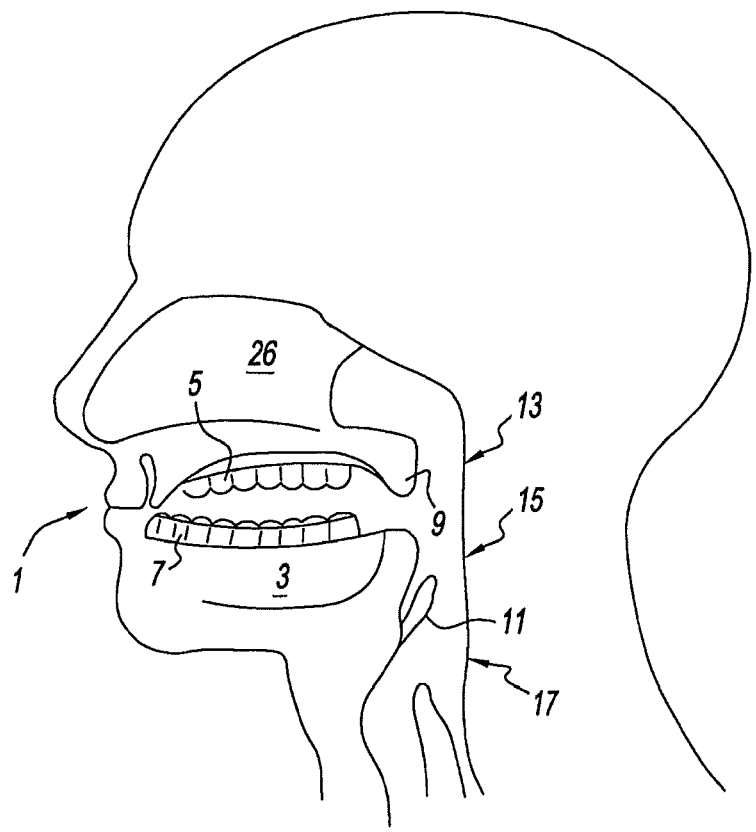
FIG. 1 is a cross-sectional view of a patient's soft palate, oral cavity and pharynx without any appliance disposed therein.

The present disclosure can best be described by referring to the figures, wherein FIG. 1 shows a cross-section of a patient's oral cavity 1. Oral cavity 1 includes a tongue 3, upper jaw 5, lower jaw 7, soft palate 9, and epiglottis 11, as well as the nasopharynx region 13, oropharynx region 15 and laryngopharynx region 17.

Figure 2:
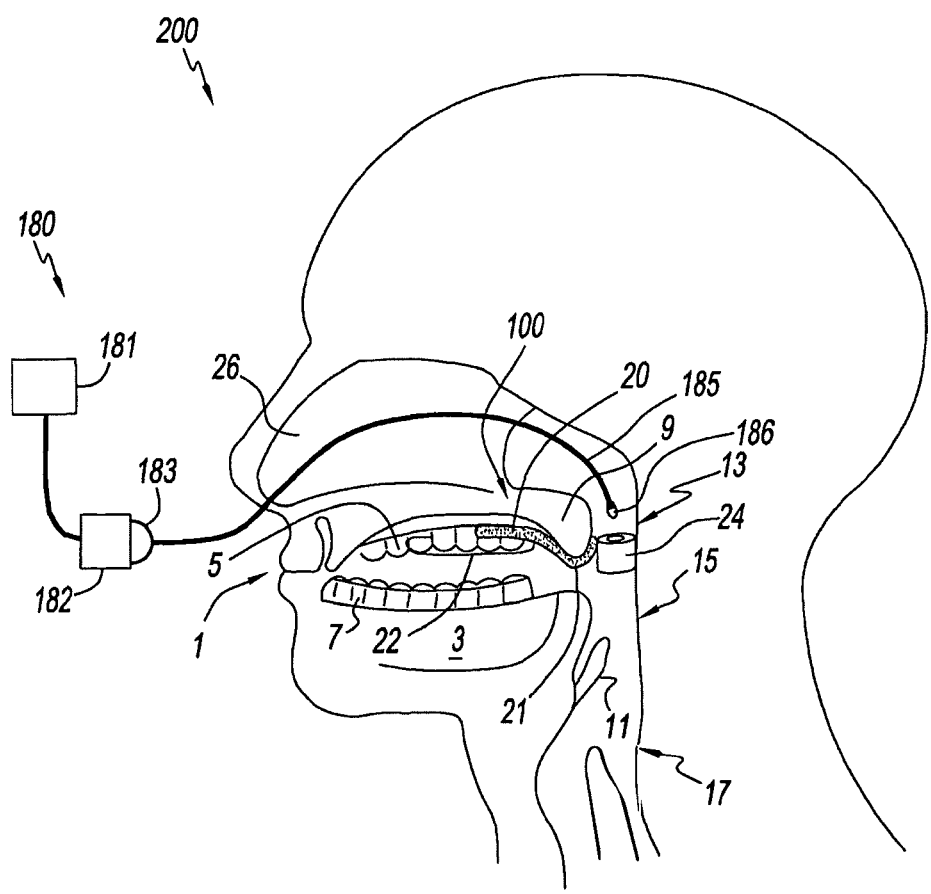
FIG. 2 is a schematic representation of a palate retainer with a tube shaped nasopharyngeal extension having a ventilation hole disposed therein, and a nasopharyngeal visualization system inserted through a nostril of a patient, according the present disclosure.

FIG. 2 depicts system 200 which comprises visualization apparatus 180 and appliance 100. Appliance 100 includes palate retainer 20 and a tube shaped nasopharyngeal extension 24. Palate retainer 20 has been positioned about the upper jaw 5 and secured thereto via a wire or other removable securing device 22, such as a wire connected to the teeth. Affixed to retainer 20 by a neck or collar portion 21 is tube shaped nasopharyngeal extension 24 which can be a solid tube with an air passageway disposed thereto to allow air to flow from the nasal passageway 26 through nasopharynx region 13 and into the oropharynx region 15 and laryngopharynx region 17. Collar portion 21 may be configured to flex, such as via an integral hinge or flexible joint, to avoid applying excessive force to tissue such as when the patient swallows. Alternatively, tube shaped nasopharyngeal extension 24 can be formed of a wire mesh or other material which is capable of permitting air to flow therethrough, while splinting soft palate 9 and tongue 3, thereby preventing soft palate 9 and tongue 3 from falling back while at the same time providing a rigid air passageway in the retropalatal and retrolingual space that cannot collapse. Extension 24 may include one or more expanding members, such as an expandable cage or balloon, configured to apply a force to maintain patience of an airway of the patient. System 200 further includes visualization apparatus 180 comprising monitor 181 which is electronically attached to camera 182. Camera 182 attaches to fiberscope 185 at jack 183. The distal end of fiberscope 185 includes lens 186, typically a fish eye or other end or side view lens configured to provide an image of the air passageways and/or inserted devices, such as an endoscopic camera commonly used in various medical procedures. Visualization apparatus 180 can be used to diagnose or prognose a patient's sleep apnea, such as when an appliance of the present invention is inserted behind the soft palate and/or the base of the patient's tongue. Alternatively or additionally, visualization apparatus 180 can be used to adjust one or more parameters of an appliance of the present invention, such as adjusting the size, geometry, exerted force, or other adjustable parameter of the appliance, described in detail herebelow. Alternatively or additionally, visualization apparatus 180 can be used to select from two or more differently configured appliances of the present invention, such as to select an appliance of appropriate geometry for a specific patient, to provide enhanced therapeutic benefit to that patient. In a system of the present invention, one appliance may have a first range of adjustability, and a second appliance may have a second range of adjustability different than the first.

Figure 3:
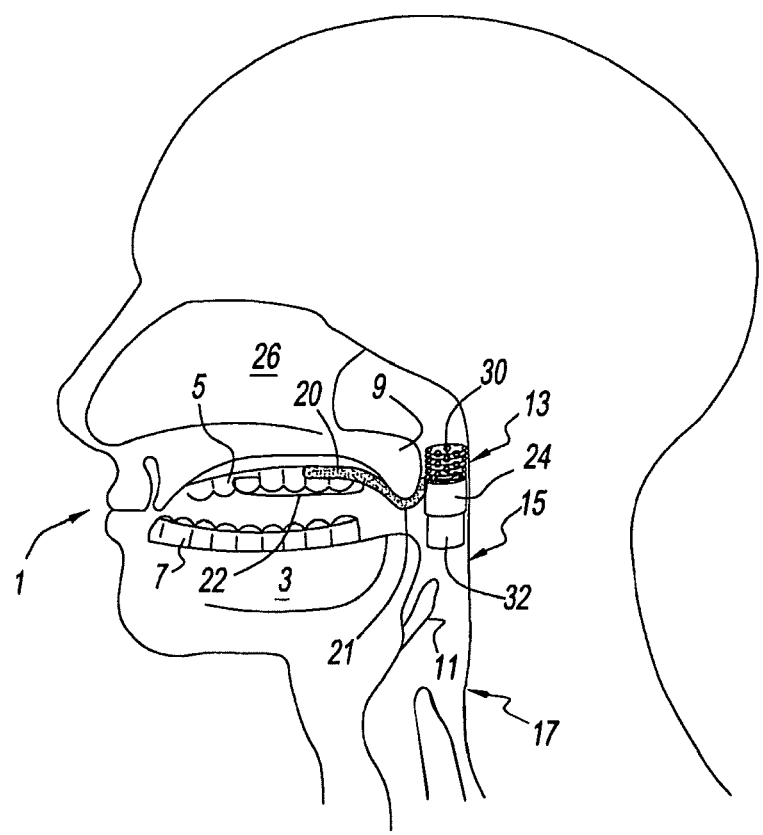
FIG. 3 is a schematic representation of the tube shaped nasopharyngeal extension of FIG. 2, wherein the tube expansible in both the upper and lower directions.

FIG. 3 demonstrates an alternative embodiment of the present disclosure wherein tube shaped nasopharyngeal extension 24 may include either an upper (superior) extension 30 or lower (inferior) extension 32. Such extensions 30, 32 can be gravity or spring actuated, and formed of materials which allow for collapsing or bending, and for easy removal from oral cavity 1 after use. Preferably, upper extension 30 is formed of a perforated material, such as wire mesh with, optionally, reinforced sections to prevent collapse, to all for air to flow therethrough. Alternatively, extension 30 can also be formed of a solid material, similar or identical to that of nasopharyngeal extension 24. Although, lower extension 32 is preferably formed of a solid material, it can also be formed of a perforated material similar to upper extension 30. Upper and lower extensions 30 and 32 have a construction including one or more air flow channels, or are made of porous or perforated materials that allow air to pass through. Having upper and lower extension (30, 32) protruding from nasopharyngeal extension 24 provides for reinforcement of the soft palate and tongue over a greater distance or length, and thereby prevents constriction between soft palate 9 and nasopharynx region 13 and/or between tongue 3 and oropharynx region 15 due to sleep apnea conditions.

Figure 4:
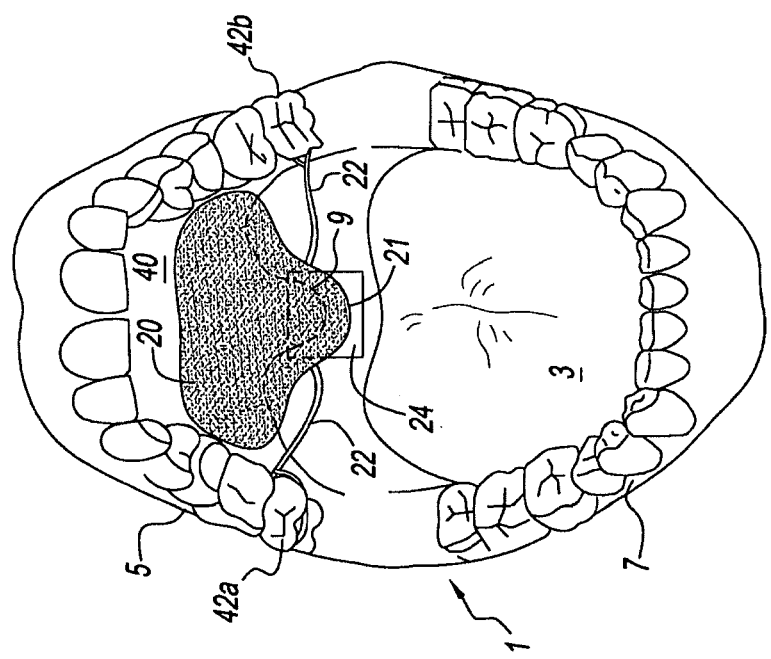
FIG. 4 is a schematic representation of the palate retainer with a tube shaped nasopharyngeal extension disposed behind the soft palate, wherein the palate retainer is secured to the teeth in the upper jaw to hold it in place.

FIG. 4 is a schematic representation of a front planar view of oral cavity 1, wherein the upper jaw 5 and lower jaw 7 are spread apart to show tongue 3, as well as the preferred positioning of palate retainer 20 about the palate 40, such that tube shaped nasopharyngeal extension 24 is disposed behind soft palate 9. FIG. 4 also shows wire or securing device 22 affixed to opposite sides of upper jaw 5 via securing wire 22 about a respective tooth 42a and 42b on each side thereof. Securing wire 22 holds palate retainer 20 in place about palate 40 such that nasopharyngeal extension 24 is securely positioned behind soft palate 9 by means of a molded collar or neck 21 disposed between retainer 20 and extension 24 to maintain an air passageway between soft palate 9 and nasopharynx region 13 and oropharynx region 13 during sleep apnea attacks. Neck 21 may be configured to flex, such as via an integral hinge or flexible joint, to avoid applying excessive force to tissue such as when the patient swallows.

Figure 5:
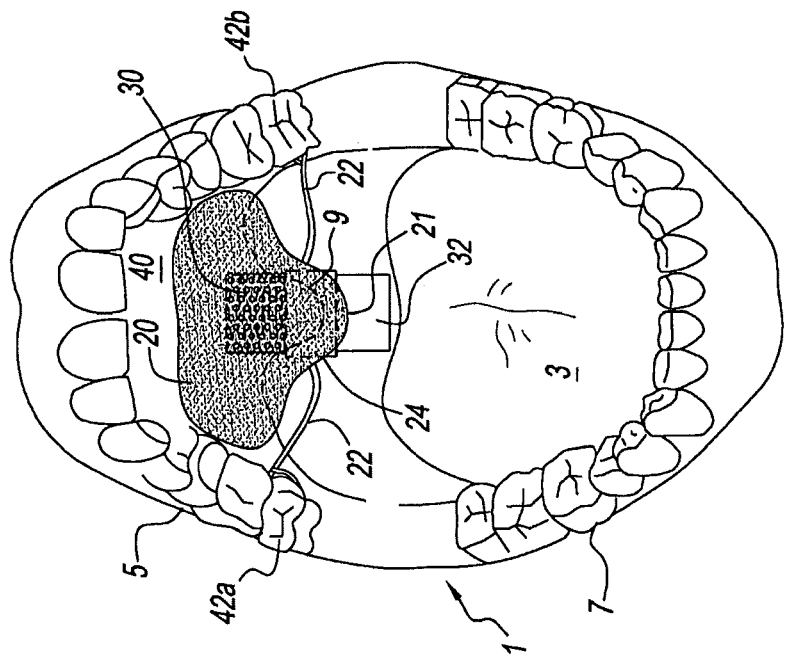
FIG. 5 is a schematic representation of the palate retainer of FIG. 4, wherein the tube shaped nasopharyngeal extension is expanded in both the upper and lower directions.

FIG. 5 is similar to FIG. 4, but demonstrates nasopharyngeal extension 24 with upper and lower extensions 30 and 32, as shown in FIG. 3. This configuration is capable of permitting air to flow therethrough, while splinting soft palate 9 and tongue 3, thereby preventing soft palate 9 and tongue 3 from falling back while at the same time providing a rigid air passageway in the retopalatal and retrolingual space that cannot collapse.

Figure 6:
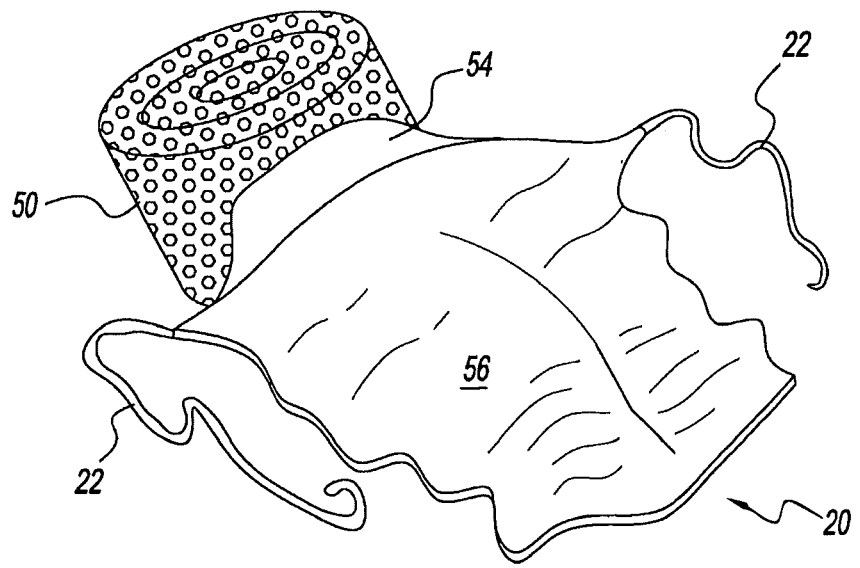
FIG. 6 is a front perspective view of a palate retainer with a perforated tube shaped nasopharyngeal extension, wherein the retainer has a retainer portion which is configured to come into contact with the soft palate of a patient.
Figure 6A:
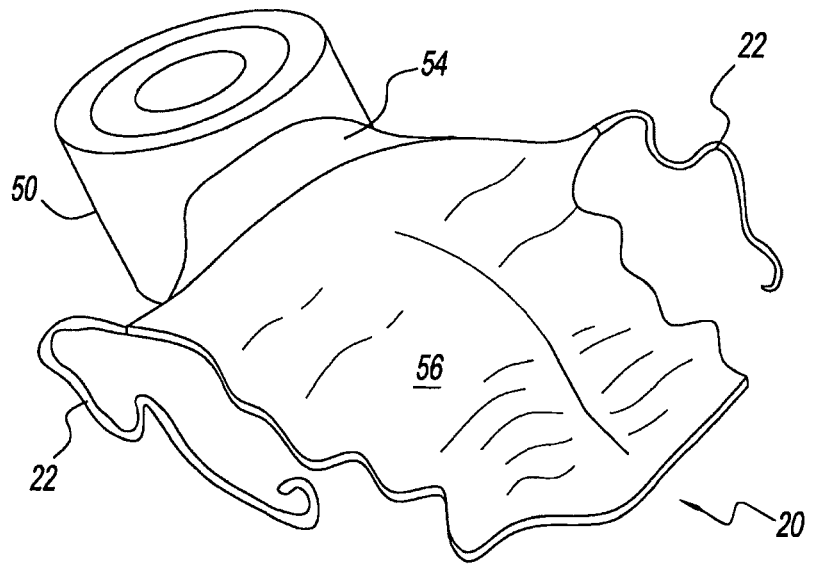
FIG. 6a is a front perspective view of a palate retainer with a solid tube shaped nasopharyngeal extension, wherein the retainer has a retainer portion which is configured to come into contact with the soft palate of a patient.

FIGS. 6 and 6a depict palate retainer 20 having a perforated and solid tube shaped nasopharyngeal extensions 50 and 52, respectively, connected thereto by support 54 which resides in front and below the soft palate. In this embodiment, retainer 20 includes a continuous retainer portion 56 which is disposed about the palate of the upper jaw, not shown. Extension 50 of FIG. 6 has a porous or perforated construction, while extension 50 of FIG. 6a has a solid tube construction.

Figure 7:
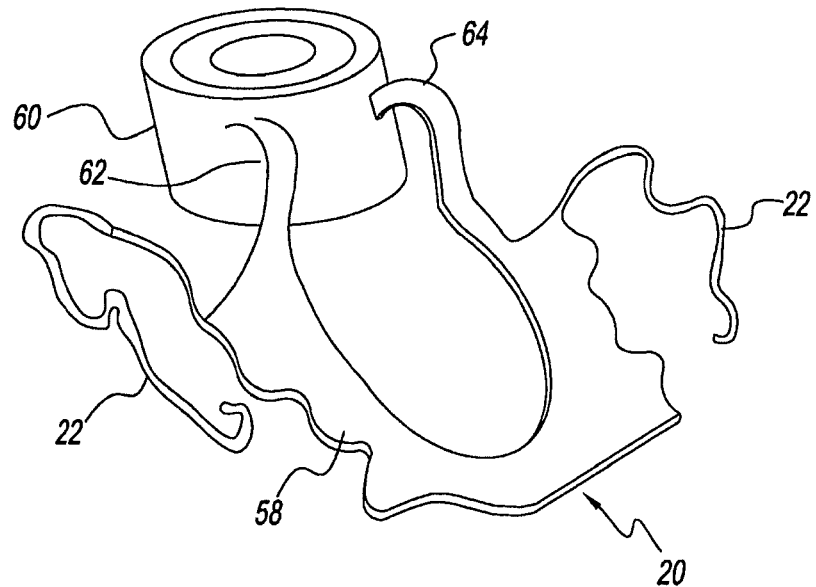
FIG. 7 is a front perspective view of a palate retainer with a tube shaped nasopharyngeal extension, wherein the retainer has a retainer portion which is configured to be affixed to the upper jaw, but not come in contact with a substantial portion of the soft palate of a patient, wherein the tube shaped nasopharyngeal extension is secured to the retainer portion by means of a pair of curved ribbons, strap, conduits, etc.

FIG. 7 is another embodiment according to the present disclosure, wherein a non-continuous retainer portion 58 is used in order to avoid substantial contact between the palate of the upper jaw and retainer portion 58, as well as the soft palate to avoid irritation or gagging due to such contact. Retainer portion 58 is secured to nasopharyngeal extension 60 via a pair of oppositely disposed arched or "C" shaped necks or collars or ribbons 62, 64 or other securing devices which bend around the sides of the soft palate to hold tube 60 behind the soft palate. Ribbons 62 and/or 64 may be configured to allow flexing between retainer 20 and extension 60, such as during swallowing.

Figure 7A:
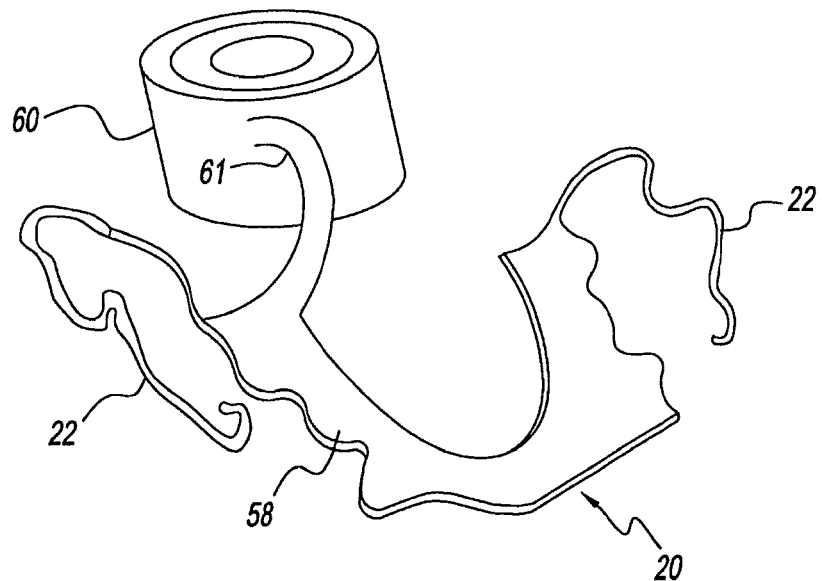
FIG. 7a is a front perspective view of a palate retainer with a tube shaped nasopharyngeal extension, wherein the retainer has a retainer portion which is configured to be affixed to the upper jaw, but not come in contact with a substantial portion of the soft palate of a patient, wherein the tube shaped nasopharyngeal extension is secured to the retainer portion by means of a single curved ribbon, strap, conduit, etc.

FIG. 7a is a front perspective view of palate retainer 20 with tube shaped nasopharyngeal extension 60, wherein retainer 20 has a retainer portion 58 which is configured to be affixed to the upper jaw, but not come in contact with a substantial portion of the soft palate of a patient, wherein tube shaped nasopharyngeal extension 60 is secured to the retainer portion by means of a single curved ribbon, strap, conduit, neck, collar, etc. 61, preferably configured to flex during swallowing.

Figure 7B:
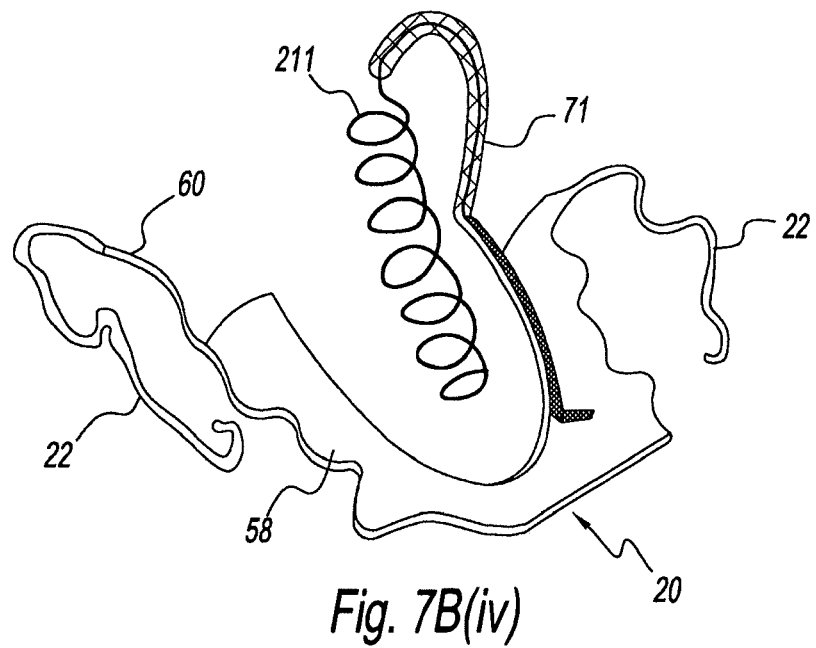
FIG. 7b(i) is yet another embodiment of the present disclosure depicting a palate retainer, wherein the retainer has a retainer portion which is configured to be affixed to the upper jaw, but not come in contact with a substantial portion of the soft palate of a patient, and wherein a stent housing in the general shape of a curved or "C" shaped tube or ribbon for housing an expandable stent therein is disposed about at least one portion of the retainer portion.
Figure 7B:
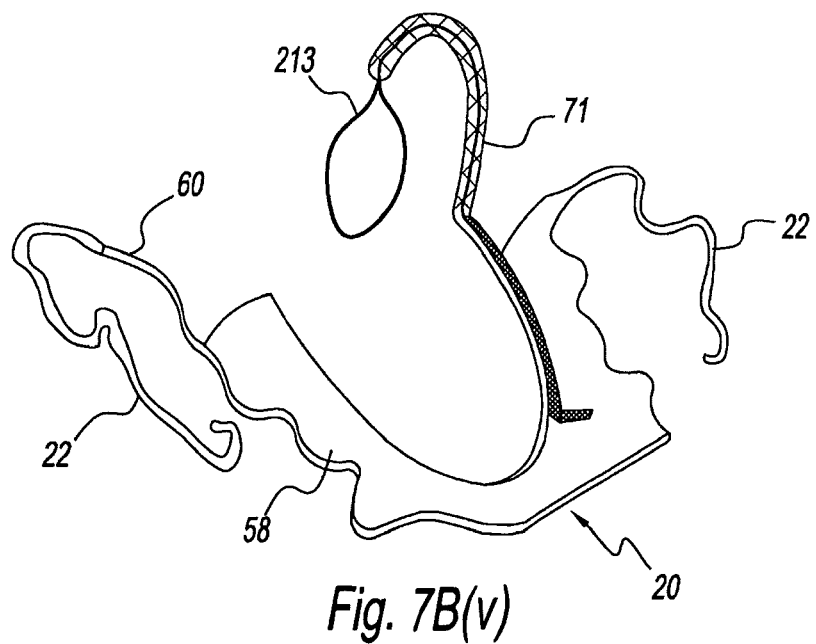

FIGS. 7b(i) and (ii) is yet another embodiment of the present disclosure depicting palate retainer 20, wherein retainer 20 has retainer portion 58 which is configured to be affixed to the upper jaw (not shown), but not come in contact with a substantial portion of the soft palate of a patient, and wherein a stent housing 71 in the general shape of a tube or ribbon for housing expandable stent 73 therein is disposed about at least one portion of retainer portion 58. FIG. 7b(ii) depicts stent 73 in the exposed or expanded position. In an alternative embodiment, a second stent housing 71 is included, not shown but preferably in a mirrored or symmetric configuration, on the opposite side of palate retainer 20, and configured to exert a force on the opposite side of the soft palate of the patient.

Alternatively, the stent of FIG. 7b(i) can be replaced with the balloons of FIGS. 7b(iii)(a)-(d), wherein (a) and (b) show a pair of balloons 201 or expandable wire balls that can be either inflated or expanded by mechanical means, not shown. FIG. 7(b)(iii)(c) depicts a pair of inflatable disks 203 encased in a wire mesh 205 according to still yet another embodiment of the present disclosure. FIG. 7(b)(iii)(d) is yet another embodiment wherein inflatable units 207 are encased in a wire mesh 209.

FIG. 7b(iv) is another embodiment wherein the stent of FIG. 7b(i) is replaced with a memory wire 211 which forms a spiral or helical configuration when exposed, such as when mechanically released or when exposed to body temperature. Memory wire 211 may comprise a resiliently biased material, such as Nitinol wire in a superelastic state or other elastic metal, alloy or plastic. Alternatively, memory wire 211 may comprise a shaped-memory material, such as a shaped memory alloy or shaped memory polymer.

FIG. 7b(v) is another embodiment wherein the stent of FIG. 7b(i) is replaced with a memory wire 213, constructed of one or more materials described in reference to memory wire 211 of FIG. 7b(iv). Memory wire 213 forms a loop or elliptical configuration when exposed, such as when mechanically released or when exposed to body temperature.

FIGS. 7c(i) and (ii) is yet another embodiment of the present disclosure depicting stent housing 71 comprising stent 73 which is preferably formed of a metal or magnetic wire mesh, and wherein at least one magnet 75, comprising a corresponding magnet or magnetic material, is disposed about retainer portion 58, thereby allowing for the soft palate (not shown) to be held in an opened position due to the magnetic force between magnet 75 and the wire mesh stent 73 disposed in the expanded position behind the soft palate. In an alternative embodiment, a second stent housing 71 is included, not shown but preferably in a mirrored or symmetric configuration, on the opposite side of palate retainer 20, and configured to exert a force on the opposite side of the soft palate of the patient. In another alternative embodiment, stent housing 71 may be a simple wire or ribbon, without an internal stent, configured to exert a force on the soft palate. The wire or ribbon may include one or more magnets or magnetic materials that exert a force on the soft palate caused by their attraction force toward a corresponding magnet or magnetic material disposed about retainer 20, disposed in a separate component of the appliance, and/or implanted in the patient. The wire or ribbon may include one or more expandable assemblies, such as one or more expandable balloons configured to exert a force on the soft palate.

Alternatively or additionally, magnets or metal wire can be implanted within the soft palate, thereby utilizing magnetic forces to move the soft palate toward magnet 75 to keep the soft palate from collapsing into the airway of the patient.

Figure 7D:
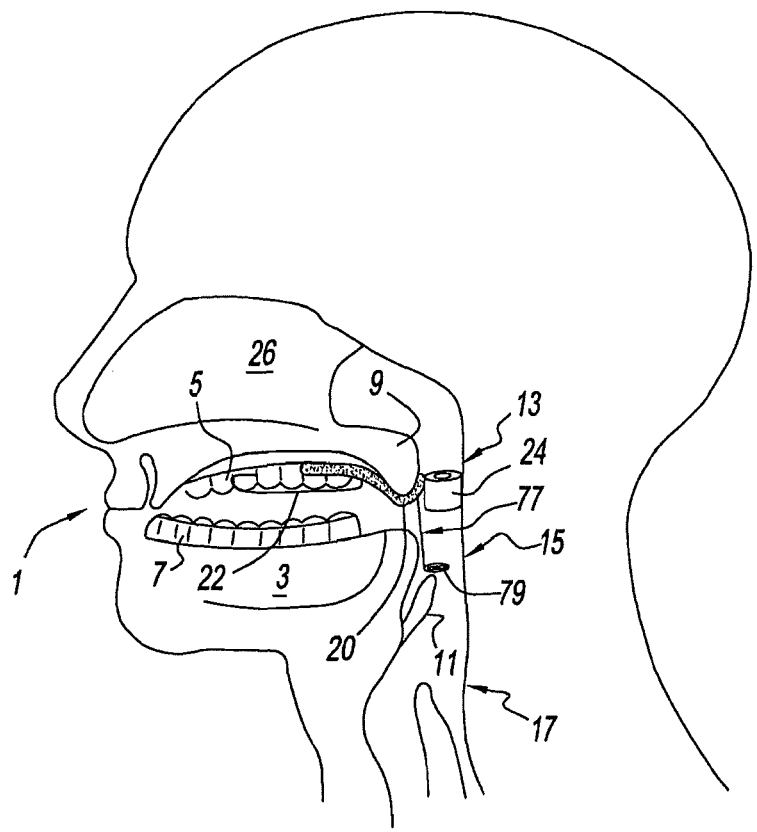

FIG. 7d is yet another embodiment according to the present disclosure and depicts a cross-sectional view of an appliance 77, wherein palate retainer 20 is a platform for both a fixed tube 24 disposed behind soft palate 9 and a downwardly expandable tube 79 disposed behind the base of a tongue 3, optionally, with a expansion bulb or the like (not shown but preferably an expandable balloon or an expandable cage). In an alternative embodiment, tube 79 is of ribbon or wire construction, such as a nitinol ribbon or other elastically biased ribbon or wire configured to apply pressure behind the tongue of the patient. Fixed tube 24 and expandable tube 79 may be attached to retainer 20 such as to allow movement such as during patient swallowing.

Optionally, the nasopharyngeal extensions are formed of a compressed flexible tube with several hard plastic rings to prevent collapse of the tube.

Figure 8:
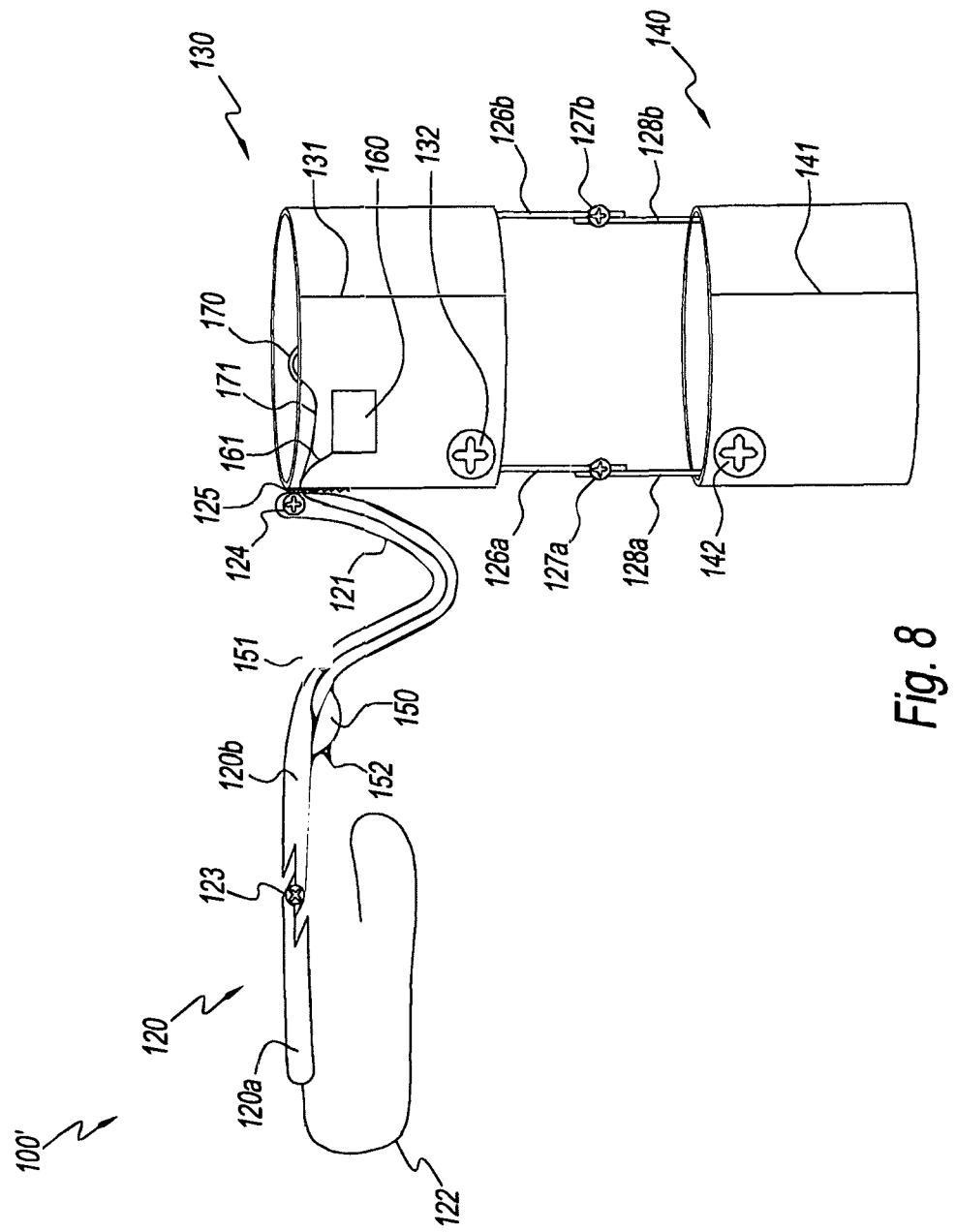
FIG. 8 is a schematic representation of a side view of an appliance according the present disclosure, wherein an adjustable palate retainer is attached to adjustable upper and lower extensions, optionally with a force transducer in communication with an electronic assembly, consistent with the present invention.

FIG. 8 demonstrates an alternative embodiment of the appliance of the present disclosure wherein appliance 100' includes adjustable palate retainer 120 which attaches to a palate extender device, adjustable upper extension 130. Upper extension 130 is adjustably attached to a base of tongue extender device, lower extension 140, which is also adjustable. Palate retainer 120 includes securing element 122, preferably two wire filaments, one on each side of the upper jaw, configured to be removably attached to the patient's upper teeth. Alternatively or additionally, appliance 100' and the other appliances of the present invention may be attached to the teeth of the lower jaw of the patient. Palate retainer 120 further includes proximal portion 120a and distal portion 120b which are adjustably attached via horizontal adjustment means 123, such as a rack and pinion or other mechanical adjustment assembly. Adjustment means 123 can be adjusted, such as via a screwdriver or other tool, to adjust the overall length of palate retainer 120. Palate retainer 120 includes, on its distal end, collar portion 121 which flexibly and adjustably attaches to upper extension 130 via vertical adjustment means 124. Vertical adjustment means includes rack 125 such that rotation of a screw of vertical adjustment means 124 causes vertical translation (e.g. rack and pinion superior and inferior adjustment) of upper extension 130 relative to palate retainer 120.

Upper extension 130 attaches to lower extension 140 via a vertically adjustable assembly comprising upper arms 126a and 126b which adjustably attach to lower arms 128a and 128b respectively. Adjustment means 127a adjustably connects upper arm 126a to lower arm 128a. Adjustment means 127b adjustably connects upper arm 126b to lower arm 128b. Adjustment means 127a and 127b each include a rotating screw or other means configured to move lower extension 140 toward or away from upper extension 130.

Upper extension 130 may include means of adjusting its outer diameter, diameter adjustment means 132, such as a screwdriver or other tool activated mechanism which causes radial expansion or contraction of upper extension 130. Adjustment can be performed prior to, during, or after placement of upper extension 130 behind the patient's soft palette. In a preferred embodiment, upper extension 130 is a wound coil, and activation of adjustment means 132 causes edge 131 to rotationally translate to increase or decrease the relative diameter of upper extension 130. Lower extension 140 may include means of adjusting its outer diameter, diameter adjustment means 142, of similar or dissimilar configuration to adjustment means 132 of upper extension 130, but preferably configured to be operably adjusted by a screwdriver or other tool to radially expand or contract lower extension 140, such as by translation of edge 141. Similarly, lower extension 140 may be adjusted prior to, during, or after placement behind the base of the tongue of the patient. In an alternative embodiment, upper extension 130 and/or lower extension 140 include one or more heat-activated components, such as one or more Nitinol components configured to expand at body temperature, such that radial expansion occurs as upper extension 130 and/or lower extension 140 transition from room temperature to body temperature (e.g. soon after placement in the patient's mouth).

Upper extension 130 may further include a sensor assembly, such as strain gauge assembly 160, configured to provide information regarding one or more patient conditions or one or more conditions of upper extension 130. Strain gauge assembly 160 attaches to electronic module 150 of palate retainer 120 via wire 161, typically a bundle of wires and/or optical fibers which attaches to wire 151, also typically a bundle of wires and/or optical fibers. Wire 151 is connected to electronic module 150. Electronic module 150 may include power, such as battery power, and signal storage and/or processing means, such as means to store and/or process the information received from strain gauge assembly 160. This information can be used to diagnose or prognose a patient's sleep apnea condition (e.g. the amount of force being applied to upper extension 130, such as during sleep where higher closing force may correspond to more severe sleep apnea), and or optimize the adjustable parameters of one or more components of appliance 100' (e.g. upper extension 130 diameter and/or vertical positioning). Electronic module 150 may include an electronic attachment port, jack 152, which allows attachment of a handheld or other electronic device which can download or upload information from or to electronic module 150. Alternatively or additionally, lower extension 140 may include a strain gauge assembly, not shown but preferably electrically connected to electronic module 150 or another electronic assembly.

Upper Extension 130 may further include a visualization element, lens assembly 170, a camera or camera lens assembly. Lens assembly 170 attaches to electronic module 150 of palate retainer 120 via wire 171, typically a bundle of wires and/or optical fibers which is attached to wire 151, also typically a bundle of wires and/or optical fibers attached to electronic module 150. Lens assembly 170 provides an image of the inner surface of upper extension 130 and the tissue surrounding upper extension 130 (e.g. the soft palate), and can be used to diagnose or prognose the patient's sleep apnea condition as well as adjust one or more parameters of appliance 100' such as the diameter of upper extension 130. Lens assembly 170 may be a CCD device used to record images, or may be a lens assembly in optical communication with a separate CCD device such as a CCD device integral to electronic module 150 or connected to electronic module 150 via jack 152. Alternatively or additionally, lower extension 140 may include a camera or lens assembly, not shown but preferably electrically connected to electronic module 150 or another electronic assembly.

Figure 9:
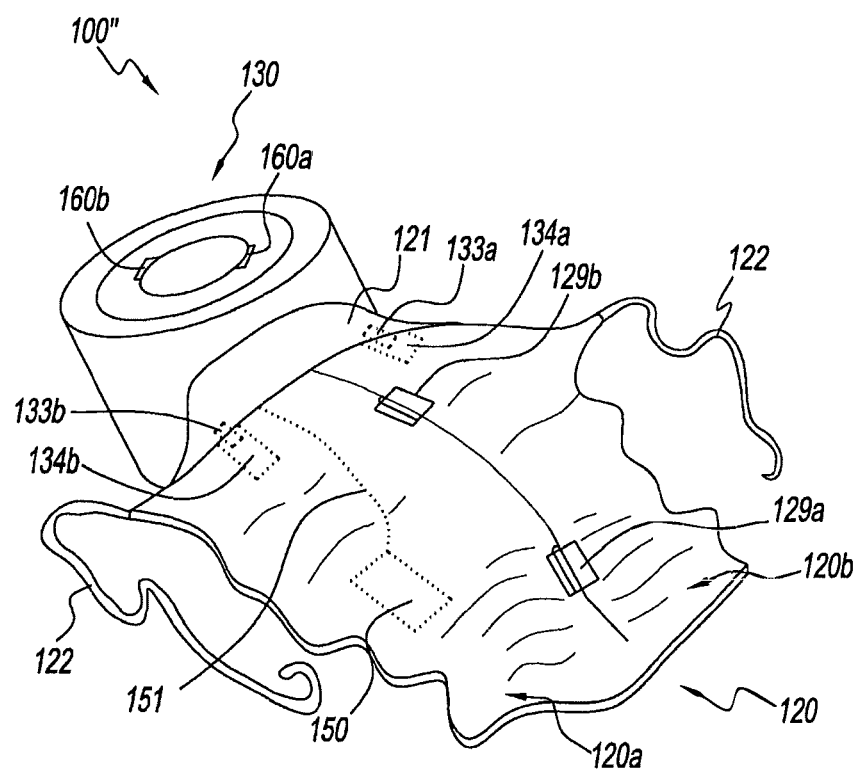
FIG. 9 is a front perspective view of an appliance according to the present disclosure, wherein a palate retainer is removably attachable to a collar portion which is attached to a tube shaped nasopharyngeal extension, wherein the retainer includes two pivotally attached portions and an electronic module in electronic communication with strain gauges integral to the nasopharyngeal extension.

FIG. 9 demonstrates an alternative embodiment of the appliance of the present disclosure wherein appliance 100" includes a hinged palate retainer 120 which attaches to a palate extender device, upper extension 130 via a detachable collar portion 121, which is configured to reside in front and below (inferior to) the soft palate and flex such that upper extension 130 can flex in relation to retainer 120. Palate retainer is configured for attachment to the teeth of the upper jaw, via securing elements 122, as has been described hereabove. Palate retainer 120 includes receiving holes 134a and 134b which slidingly receive projecting pins 133a and 133b respectively, of collar portion 121, such that palate retainer 120 can be attached to collar portion 121 after upper extension 130 is in place behind the patient's soft palate. In an alternative embodiment, appliance 100" may include multiple assemblies including collar portion 121 and upper extension 130, each configured to attach to a single palate retainer 120. Multiple sets of upper extension 130 and collar portion 121 may be useful in diagnosing and/or treating a patient's sleep apnea, such as when each set is of different construction (e.g. diameters, biasing forces, and other geometric and physical properties).

Palate retainer 120 includes two halved portions 120a and 120b which are rotatably connected via hinges 129a and 129b, such that palate retainer 120 can be folded when collar portion 121 is not attached. Palate retainer 120 further includes electronic module 150 which is electrically connected to wire 151, typically one or more wires and/or fiber optic cables. Wire 151 attaches to strain gauges 160a and 160b of upper extension 130. Forces recorded by strain gauges 160a and 160b are received and preferably recorded by electronic module 150, as has been described above in reference to FIG. 8, to diagnose, prognose, and/or modify treatment of a patient having or suspected of having sleep apnea.

Figure 10A:
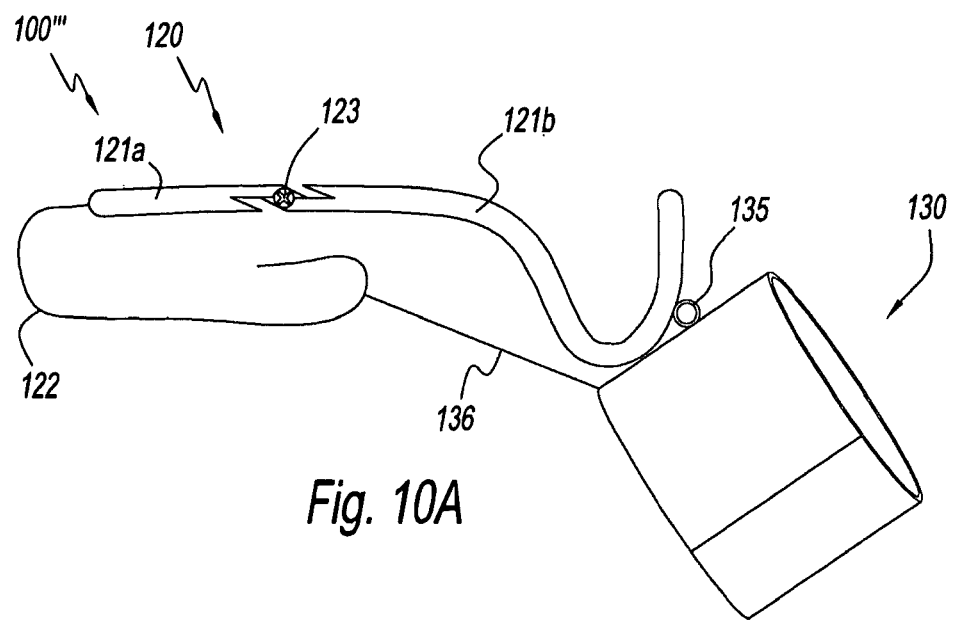
FIG. 10A a schematic representation of a side view of an appliance according to the present disclosure, wherein an upper extension is rotatably attached to the palate retainer, maintained in a pre-deployed position by a band.
Figure 10B:
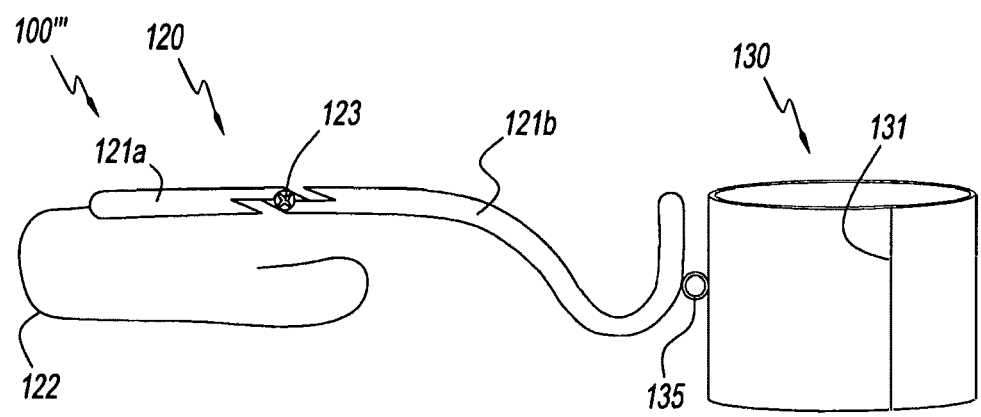
FIG. 10B is a schematic representation of the side view of the appliance of FIG. 10A wherein the band has been removed and the upper extension has rotated into a deployed position.

FIGS. 10A and 10B demonstrate an alternative embodiment of the appliance of the present disclosure wherein appliance 100''' includes an adjustable length palate retainer 120 which is rotatably attached to upper extension 130. Palate retainer 120 includes securing elements 122 (one shown in side view but preferably one on each side) which attach palate retainer 120 to the teeth of the patient's upper jaw. Palate retainer 120 includes, on its distal end, collar 121, which is configured to reside in front and below (inferior to) the soft palate of the patient. Collar 121 attaches to a palate extender device, upper extension 130 via spring loaded hinge 135.

Referring specifically to FIG. 10A, upper extension 130 is biased in a pre-deployed position by band 136 preferably of a rubber band or similar elastically biased construction connected the bottom portion of upper extension 130 to one or more securing elements 122, such as via one or more hooks on upper extension 130 and/or securing elements 122, that engage looped ends of band 136, hooks and loops not shown. In an alternative embodiment, a gentle detachment or tearing force is applied to remove band 136 from securing element 122 and/or upper extension 130. In the configuration of FIG. 10A, appliance 100''' can be easily inserted into the patient's mouth, and securing elements 122 attached to the teeth of the patient's upper jaw.

Once in place, band 136 can be detached from either or both securing element 122 and upper extension 130, allowing upper extension 130 to rotate to a position applying a biasing force to the patient's soft palate, in the configuration of FIG. 10A, patient's anatomy not shown but described in detail hereabove. In a preferred method, band 136 is removed from securing element 122 first, and slow manual translation of the band toward the back of the patient's throat causes a slow deployment of upper extension 130 to be located behind and apply a force to the soft palate of the patient. Once in place, band 136 can be removed from upper extension 130 as has been described above.

Figure 11:
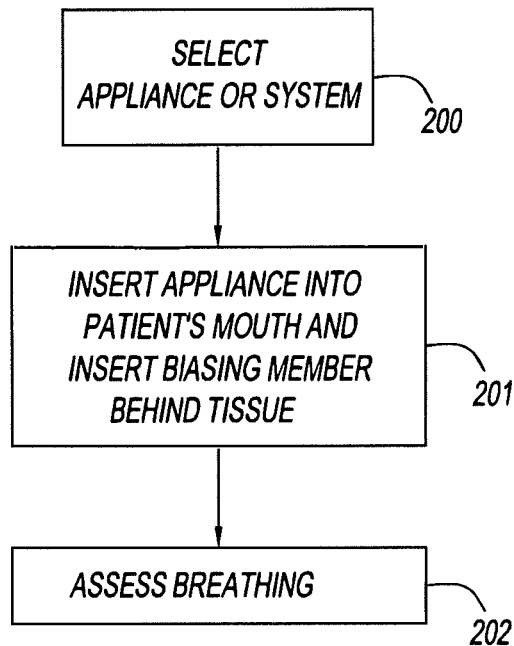
FIG. 11 is a flow chart of a preferred method of diagnosing a patient suspected of having sleep apnea using an appliance of the present disclosure.

FIG. 11 demonstrates a preferred method of diagnosing a patient known to have or suspected of having sleep apnea. In Step 200, an appliance or system of the present invention is selected. The appliance selected may include one or more diagnostic or sensing capabilities such as the force measurement capabilities of an appliance of the present invention, such as the appliances 100' or 100" of FIG. 8 or 9, respectively. The appliance selected may be a system of the present invention, such as system including two or more different appliances, or a system including a visualization instrument, such as system 200 of FIG. 2, and an appliance of the present invention.

In Step 201, the appliance is inserted into the patient's mouth, and a extender device of the appliance is placed behind the soft palate and/or behind the base of the patient's tongue. At this time, one or more other devices may be inserted into the patient, such as visualization instrument 180 of FIG. 2, or put in a position to monitor one or more parameters of the patient, such as EEG or EKG electrodes, respiration monitors, snoring monitors, sound monitors, and other physiologic measuring sensors and/or devices used to diagnose, prognose or otherwise assess a sleep apnea patient.

In Step 202, the patient's breathing is assessed, such as by using the one or more diagnostic instruments described in reference to Step 201 above. In a preferred embodiment, the assessment includes a period of time when the patient is asleep. The assessment may include comparison to similar testing performed without an appliance of the present invention in place in the patient, or with a differently configured appliance used. The assessment phase may include adjusting one or more parameters of the appliance, such as to modify the magnitude of a biasing force applied to the soft palate and/or the base of the tongue. The assessment may include a comfort assessment, such as comfort assessed through measurement of physiologic parameters or by completing a patient questionnaire.

Figure 12:
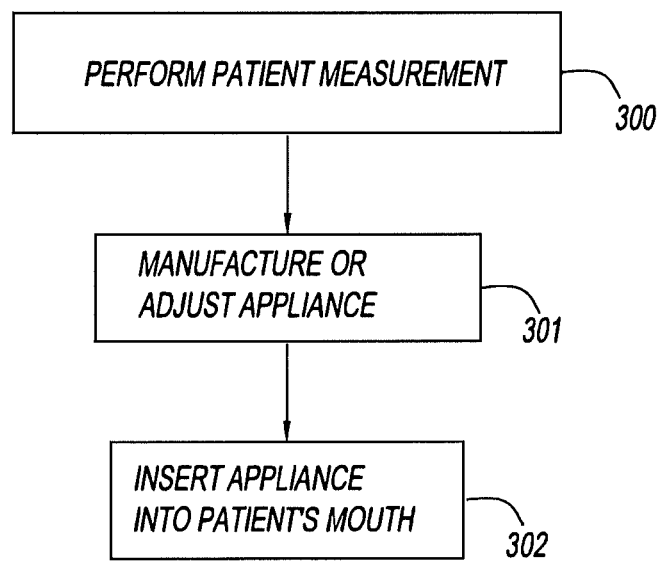
FIG. 12 is a flow chart of a preferred method of manufacturing an appliance of the present disclosure.

FIG. 12 demonstrates a preferred method of manufacturing or adjusting an appliance of the present invention for a particular patient known to have or suspected of having sleep apnea. In Step 300, a patient assessment is performed such as a diagnostic procedure performed while the patient is sleeping. The assessment may include the creation of one or more images used to determine the proper dimensions of the appliance, such as images created with technologies such as x-ray, CT scan, Mill, ultrasound, and other imaging technologies commonly found in health care centers. The imaging may be created by a camera, such as a camera inserted to the areas behind the patient's soft palate and tongue (e.g. imaging scopes entered through the nose and/or the mouth), wherein visible light pictures are used to measure the patient's anatomy.

Step 301 includes the manufacture or adjustment of an appliance of the present invention based on the patient measurements performed and/or other data collected in Step 300. This manufacture of a new appliance, and/or adjustment of an existing appliance, allows patient-specific treatment of a particular patient's sleep apnea and yields improved comfort for the patient (with an inserted device), as well as better efficacy in treatment. Patient specific sizing of the extender devices (soft palate and/or base of tongue force exerting members) can be customized to apply a sufficient force to maintain proper airflow, without applying unnecessary force. Extender device geometry can be chosen to apply force where beneficial, and avoid tissue contact that is unnecessary. Non-circular profiles, such as crescent profiles, can be used for extender devices to avoid contact with tissue to which no force application is desired. This avoidance of skin contact can be particular important on the certain surfaces of the airways, such as some anterior airway surfaces, on which swallowing and gag reflexes are most sensitive.

While we have shown and described several embodiments in accordance with our invention, it is to be clearly understood that the same may be susceptible to numerous changes apparent to one skilled in the art. Therefore, we do not wish to be limited to the details shown and described but intend to show all changes and modifications that come within the scope of the appended claims. In addition, each of the drawings are not to scale, but are simply representative drawings to assist in the understanding of the present disclosure.

What is claimed is:

1. A method for diagnosing sleep apnea in a patient, said method comprising:
   inserting into a mouth of a patient a medical appliance which comprises: a securing device configured to be removably affixed to a jaw of said patient; a biasing member which is insertable behind a soft palate and/or a base of a tongue of said patient wherein said securing device is connected to said biasing member to allow insertion and/or removal of said biasing member from the nasopharyngeal airway; and
   a force measurement assembly; and
   conducting at least one diagnostic procedure including:
   (a) measuring, by the force measurement assembly, a force exerted by said biasing member upon said soft palate or base of said tongue of said patient, wherein conducting the at least one diagnostic procedure is further selected from the group comprising:

(b) viewing the amount of contact between said biasing member and said soft palate or base of said tongue of said patient;

(c) inserting a visualization assembly into said mouth or nose of said patient, wherein said visualization assembly is configured to visualize the amount of contact between the biasing member and said soft palate or base of said tongue of said patient; and (d) quantifying the size of the opening between said biasing member and said soft palate or base of the tongue of said patient.

2. The method according to claim 1, wherein the method further comprises monitoring one or more patient parameters via one or more devices selected from the group consisting of: electroencephalogram (EEG) or electrocardiogram (EKG) electrodes; respiration monitors; snoring monitors; and sound monitors.

3. The method according to claim 1, wherein the method further comprises assessing the patient's breathing when the medical appliance is inserted in the patient's mouth.

4. The method according to claim 3, wherein assessing the patient's breathing includes a period of time during which the patient is asleep.

5. The method according to claim 3, wherein the method further comprises assessing the patient's breathing when the medical appliance is not inserted in the patient's mouth, and wherein the patient's breathing with and without insertion of the medical application is compared.

6. The method according to claim 1, wherein the method further comprises adjusting one or more parameters of the medical appliance when inserted in the patient's mouth.

7. The method according to claim 6, wherein a magnitude of a biasing force applied to the soft palate and/or base of the tongue is modified.

8. The method according to claim 1, wherein the method further comprises assessing the patient's comfort when the medical application is inserted in the patient's mouth.

9. The method according to claim 8, further comprising a physiologic measuring sensor inserted into the patient that measures physiological parameters of the patient.

10. The method according to claim 8, wherein the patient's comfort is assessed via a patient questionnaire.

11. The method according to claim 1, wherein the biasing member comprises a stent.

12. The method according to claim 1, wherein the biasing member comprises a memory wire.

13. The method according to claim 12, wherein the memory wire has a spiral or elliptical shape when expanded.

14. The method according to claim 1, wherein the biasing member is at least one member selected from the group consisting of: a flexible or rigid stent, a balloon, a memory wire, a tube, and a combination thereof.

15. The method according to claim 1, wherein the securing device is attached to either an upper or lower jaw of the jaw of the patient.

16. The method according to claim 1, wherein the biasing member is configured to provide flow of air in the nasopharyngeal passageway.

17. The method according to claim 1, wherein the force measurement assembly is a force transducer selected from the group consisting of: a strain gauge; a magnetic sensor; a capacitive sensor; a piezo transducer; and combinations thereof.

18. The method according to claim 17, wherein the medical appliance further comprises a force monitor assembly, and wherein the diagnostic procedure comprises the force monitor assembly monitoring the measured forces to determine if the measured force exceeds a threshold.

19. The method according to claim 1, wherein the medical appliance comprises the visualization assembly, and wherein the diagnostic procedure comprises imaging the area behind the soft palate and/or area behind the base of tongue using the visualization assembly.

20. The method according to claim 19, wherein the visualization assembly is at least one of integral to the biasing member, affixed to the securing device, or in communication with the securing device via an optical fiber which is passed through said patient's nasal passage.

21. The method according to claim 1, wherein the visualization assembly comprises at least one fiber optic cable and at least one device selected from the group consisting of: a camera; a camera lens; a charge-coupled device (CCD) assembly; and combinations thereof.

* * * * *